(12) United States Patent
Wagner

(10) Patent No.: US 7,735,353 B2
(45) Date of Patent: Jun. 15, 2010

(54) METHOD AND APPARATUS FOR OSCILLATING A TEST SAMPLE

(75) Inventor: Jeff Wagner, Washington Township, Morris County, NJ (US)

(73) Assignee: Rudolph Research Analytical, Hackettstown, NJ (US)

( * ) Notice: Subject to any disclaimer, the term of this patent is extended or adjusted under 35 U.S.C. 154(b) by 385 days.

(21) Appl. No.: 11/471,355

(22) Filed: Jun. 20, 2006

(65) Prior Publication Data

US 2007/0289377 A1    Dec. 20, 2007

(51) Int. Cl.
    *G01N 9/00* (2006.01)
(52) U.S. Cl. ..................... 73/32 A; 73/24.05
(58) Field of Classification Search ............. 73/32 A, 73/32 R, 24.05, 30.01
    See application file for complete search history.

(56) References Cited

U.S. PATENT DOCUMENTS

| | | | | |
|---|---|---|---|---|
| 3,603,137 A | * | 9/1971 | Banks | 73/32 R |
| 4,199,264 A | * | 4/1980 | Uebel | 366/123 |
| 4,711,132 A | * | 12/1987 | Dahlin | 73/861.356 |
| 4,838,084 A | * | 6/1989 | Leopold et al. | 73/32 A |
| 5,237,853 A | * | 8/1993 | Cassaday et al. | 73/32 A |
| 5,339,258 A | * | 8/1994 | Stabinger et al. | 702/50 |
| 5,477,726 A | * | 12/1995 | Stabinger et al. | 73/32 A |
| 6,431,530 B1 | * | 8/2002 | Stamps et al. | 267/136 |
| 7,559,300 B2 | * | 7/2009 | Ruggiero | 123/90.12 |
| 2006/0201260 A1 | * | 9/2006 | Drahm et al. | 73/861.357 |
| 2009/0139349 A1 | * | 6/2009 | Drahm et al. | 73/861.357 |

* cited by examiner

*Primary Examiner*—Hezron Williams
*Assistant Examiner*—Samir M Shah
(74) *Attorney, Agent, or Firm*—Kaplan Gilman & Pergament LLP

(57) ABSTRACT

A method and apparatus for imparting oscillatory motion on a test sample is disclosed in which oscillators, preferably in tubular form, are surrounded by housings. An actuator causes deforming of the housings, and the deforming movement is linked to the oscillators.

16 Claims, 4 Drawing Sheets

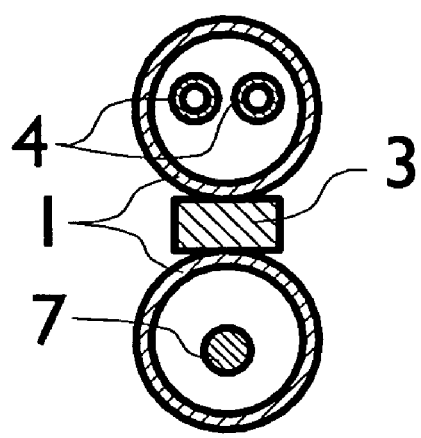
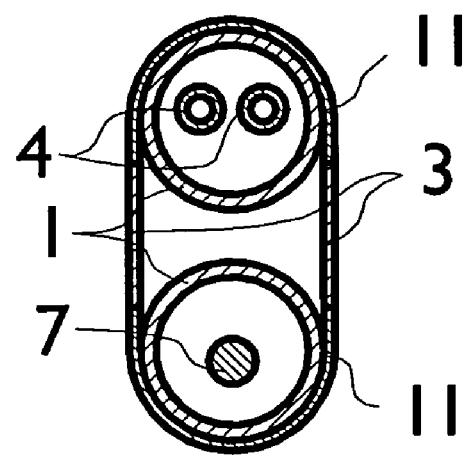
FIG. 3
FIG. 4
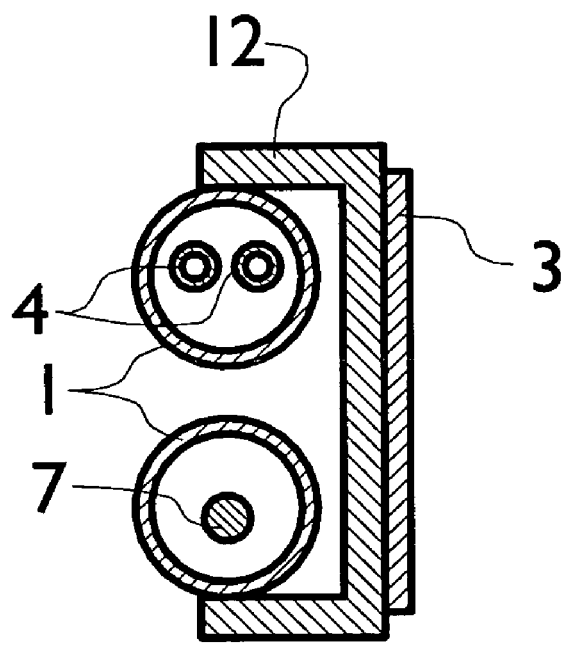
FIG. 5

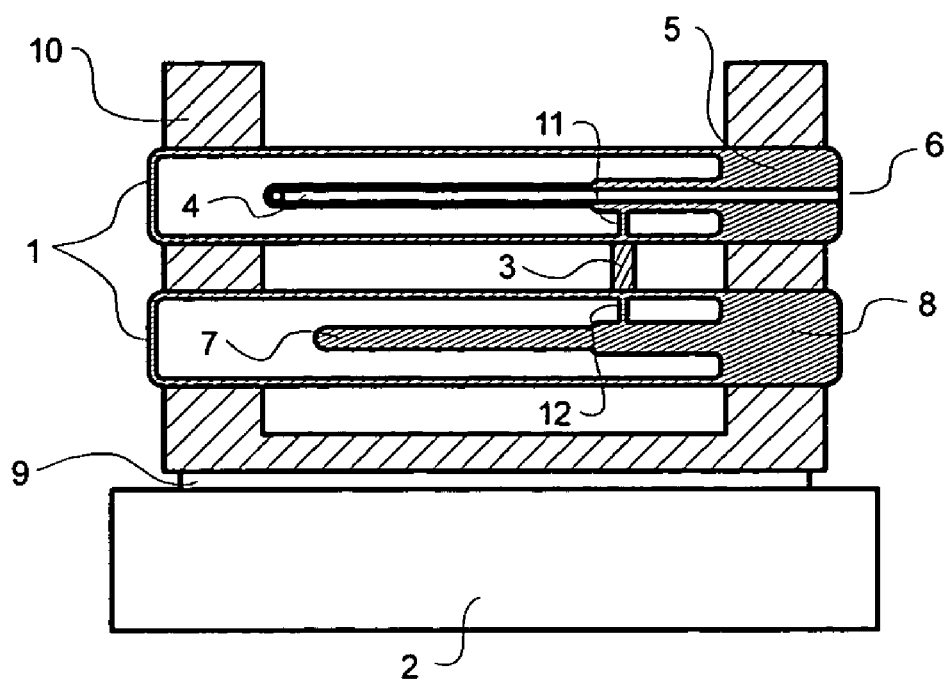
FIG. 6 (updated)
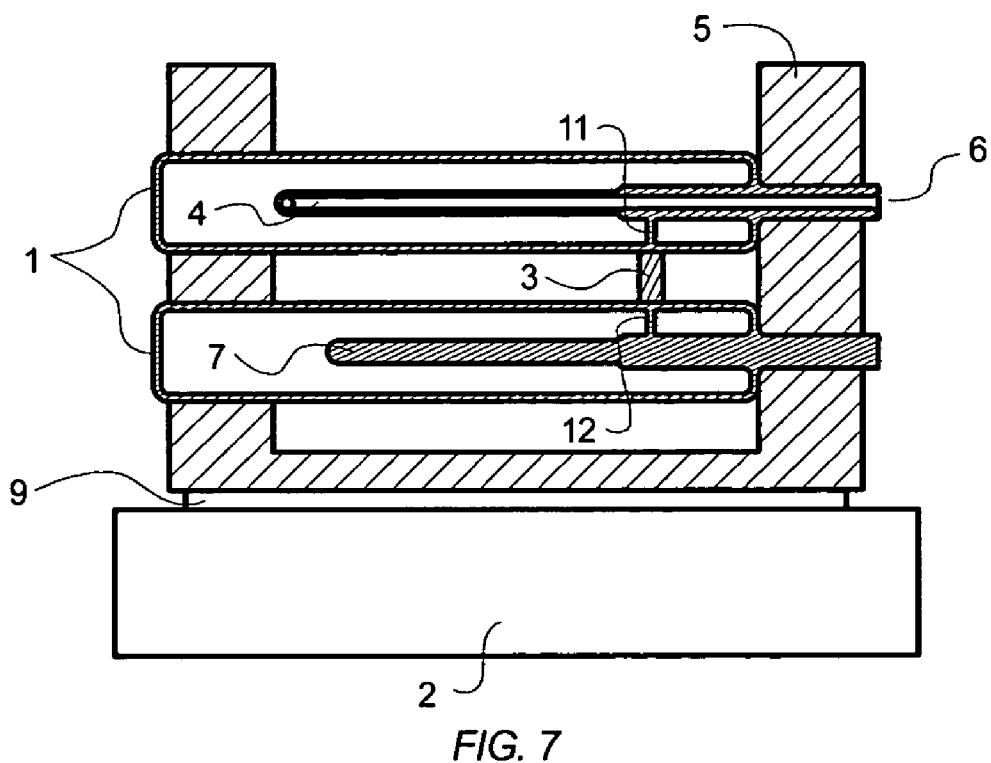
FIG. 7

METHOD AND APPARATUS FOR OSCILLATING A TEST SAMPLE

BACKGROUND OF THE INVENTION

This invention relates to devices to oscillate a test sample, and more specifically, to a device that oscillates a test sample for use in determining the density of fluids using a hollow oscillator filled with the sample under test. The method and apparatus hereof can be used to impart and maintain Devices to measure the density of a fluid mixture by oscillating the mixture within a container (i.e.; oscillator) and observing the period of oscillation are known. These devices typically include four main parts: an oscillator, an actuator, a support, and a countermass. The actuator powers the oscillation of the oscillator, which is typically filled with the fluid to be tested. A support holds the oscillator for oscillation, and a countermass provides a stable surface with respect to which the oscillator is oscillated. An example of such a device is shown in Stabinger, et al U.S. Pat. No. 5,477,726, discussed more fully below.

Several techniques of accomplishing the above are taught in the prior art. A magnet may be attached to the oscillator and driven by nearby fixed coils as taught, for example, by Janssen, U.S. Pat. No. 3,728,893. Alternately, the coil wire may be mounted on the oscillator and the magnet fixed as taught by Albert, et al in U.S. Pat. No. 4,655,075. The oscillator itself may be made of a conducting material so as to serve as a single turn coil driven by a fixed magnet as disclosed by Herrero-Alvarez in Rev. Sci. Instrum. 68 (10), October 1997.

In these techniques the actuator or a part of the actuator is mounted directly on the oscillating element. This can have number of practical disadvantages:

First, heat generated in the actuator is readily transmitted to the sample under test. Because the density of the sample under test is generally a function of temperature, an error is introduced.

Second, the mass of the portion of the actuator attached to the oscillator adds to the oscillating mass of the system. Increasing the total oscillating mass relative to the mass of the sample under test within reduces the sensitivity of the device. Additionally, as taught by Kratky et al in U.S. Pat. No. 3,910, 101, non-linearity in the relation of density to the square of the period grows with the ratio of oscillating mass to counter mass. Physically, this happens when motion induced into the counter mass moves the nodes that define the volume of the sample under test.

It is common practice to calibrate density measuring instruments with two known samples, often dry air and water. With only two calibration points any non-linearity compromises the accuracy of the measurement of densities that differ from the calibration points. Consequently an increase in the total oscillating mass requires either a much greater increase in the counter mass of the system to preserve accuracy or a further means of compensating for insufficient counter mass as disclosed, for example, by Kratky.

Third, it is advantageous to control the environment surrounding the oscillator by enclosing it within a hermetically sealed housing. Having actuator components within the housing complicates manufacture and repair.

One possible means to avoid the practical disadvantages listed above is to impart the vibratory motion not to the oscillator itself, but rather to a member to which the oscillator is attached. An example of this was disclosed by Muramoto in U.S. Pat. No. 4,132,110 in which a piezoelectric actuator introduces motion into a member attaching the ends of two parallel oscillating tubes. Beneficially, the mass of the actuator does not contribute to the mass of the oscillators. However, mounting the actuator on connector between the oscillators still creates a short thermal path into the sample under test. Also of interest in this device is the fact that the two oscillators move in opposition thereby eliminating the need for a counter mass.

A later example of introducing the vibratory motion through a member to which the oscillator attaches is taught in Stabinger, et al U.S. Pat. No. 5,477,726. Two embodiments are disclosed. In the first, the actuator is mounted between the counter mass and a thermostatically controlled housing within which the oscillator is supported. In the second embodiment the housing is eliminated and the actuator acts directly on the support of the oscillator. As in Muramoto, connecting the actuator to the support of the oscillator creates a path for heat from the actuator to flow readily into the sample under test unless further temperature control means are employed.

Although the first embodiment of Stabinger does prevent heat generated in the actuator from reaching the sample under test, another aspect of the apparatus is consequently compromised. The mass driven relative to the counter mass, consisting of the housing, temperature control means, and the oscillator supported within, is very large. For a bench top installation, where the total mass must be limited, a high ratio of oscillating mass to counter mass cannot be achieved. Consequently, the entire apparatus is in motion and provides no convenient mounting points which can be fixed without risk of influencing the oscillation. Mechanical suspensions or other further means to control and compensate for the resulting motion of the counter mass are then required.

Stabinger teaches that the temperature control means, which in his preferred embodiments are Peltier devices, are to be placed between the actuator and the oscillator. To function effectively, Peltier devices, which essentially are heat pumps, must be in intimate thermal contact with a large thermal reservoir such as the counter mass. Mounting the Peltier devices between the oscillator and actuator isolates the devices from the counter mass. Heat must then be pumped through the actuators. Piezoelectric actuators are constructed of ceramic materials and have a low thermal conductivity. Consequently, the thermal performance of this configuration is compromised.

A further disadvantage of both embodiments of Stabinger is that the entrance and exit ports of the oscillating tube translate with the actuation of the oscillator. This requires that any ancillary equipment connected to the ports be sufficiently compliant so as not to influence or restrict the action of the actuator. Vibratory motion imparted to equipment connected to the moving ports can also excite parasitic resonant vibration into the attached equipment. Parasitic resonance is a known source of error in the art.

In light of the disadvantages of the prior art, there exists a need for a density measuring apparatus that is free from temperature induced error, that is inherently linear in measurement, that can be effectively temperature controlled and that can be conveniently mounted to fixed objects such as benching, piping or other accessory equipment.

SUMMARY OF THE INVENTION

As has been noted, placing additional elements between the oscillator support and the actuator to reduce actuator heat induces errors and increases the total driven mass. Conversely, achieving a high counter mass to driven mass ratio seems to require a minimal driven mass. This apparent contradiction is resolved in the present invention.

It is an object of the present invention to provide an apparatus which determines the density of a fluid using a hollow oscillator filled with the sample under test wherein the prior art disadvantages of actuator heating are overcome by not connecting the actuator either directly to the oscillator or its support.

It is a further object of the present invention to provide an apparatus of greater inherent linearity by minimizing the motion induced into the counter mass by unbalanced masses driven relative to the counter mass.

It is a further object of the present invention to provide an apparatus in which the prior art disadvantages of placing the temperature control means between the actuator and oscillator are overcome by placing the temperature control means in direct thermal contact with the counter mass which allows the counter mass to serve as a thermal reservoir.

It is a further object of the present invention to provide an apparatus with substantially stationary mounting points, easily mountable to fixed benching, wherein the entrance and exit ports do not translate with the actuator but remain substantially fixed in position so that accessory equipment may be conveniently attached.

It is a still further object of the present invention to provide an apparatus which cooperatively with the above improvements includes a second reference oscillator, of the type disclosed, for example, by Senda in U.S. Pat. No. 3,729,982, for improving the accuracy of measurements made at temperatures differing from the calibration temperature. This second oscillator allows for correction of effects due to temperature dependant properties of the oscillator material.

One or more of the foregoing disadvantages are solved by placing the actuator in contact with a housing, causing the actuator to periodically deform the housing, and coupling the periodic deformities to the oscillator to oscillate a test sample. The actuator is preferable removed from contact with the support.

Further characteristics of the present invention are given in detail hereafter with reference to the accompanying drawings.

BRIEF DESCRIPTION OF THE DRAWINGS

FIG. 3 depicts a cross section through the compliant housing, actuator, and oscillator;

FIG. 4 depicts a cross section through an embodiment with an alternate actuator arrangement;

FIG. 5 depicts a cross section through an embodiment with a second alternate actuator arrangement;

FIG. 6 depicts a schematic view of a third embodiment of the invention in which the supports of the oscillator are rigidly mounted and motion is imparted to the oscillators by actuators comprising flexible links;

FIG. 7 is an alternative embodiment of the present invention; and

DETAILED DESCRIPTION OF THE PREFERRED EMBODIMENTS

Figure 1:
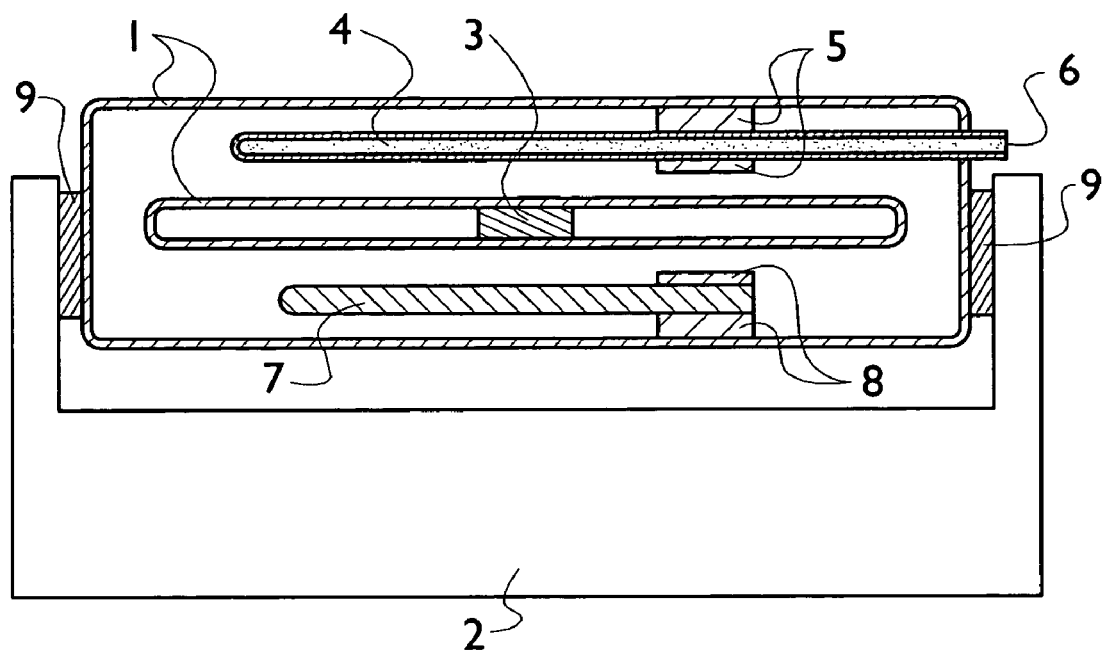
FIG. 1 depicts a schematic view of a first embodiment of the invention in which the oscillators are disposed within a single compliant housing.

Referring now to FIG. 1, a piezoelectric actuator 3 is disposed between symmetric halves of a compliant hermetic housing 1 made of any suitable material such as glass. The housing 1 is rigidly fixed by suitable means through Peltier devices 9 to counter mass 2. Disposed within the upper half of housing 1 is a hollow oscillator 4 mounted on support 5. Hollow oscillator 4 is preferably a tube formed in the shape of a letter U, viewed edgewise in the figure such that only one of the two ports 6 is visible. Ports 6 allow for introduction and removal of samples under test. Disposed within the lower half of housing 1 is reference oscillator 7 mounted on support 8.

It is preferred that the points of contact between the actuator and the housing not be directly adjacent the connections between the housing and the oscillator supports. A connection between the actuator and the oscillator support creates a path for actuator heat to flow readily into the sample under test as for example in the apparatus of Muramoto. For further improvement a means for thermal conduction, such as a copper braid, may be used to lead waste heat from the actuator to a convenient heat sink.

Not shown in the figure, but well known in the art, are means to detect the motion of each oscillator. Such means may, for example, be a beam of light periodically occluded by the motion of the oscillator. A signal derived from the combined motion of each oscillator is provided to the actuator. Although each oscillator will receive through the housing and support the vibratory input intended for both oscillators, each oscillator acts as a mechanical filter and will preferentially absorb energy only near its own natural frequency. Note that because the actuator is not disposed against the counter mass that the motion of the symmetric housing halves is in opposition. This opposed motion does not result in motion of the center of mass of the apparatus or any net torque about the center of mass. Only the motion of the cantilevered portions of the oscillators and the sample under test need be offset by the counter mass.

Also not shown in the figure, but well known in the art, are temperature measurement means which cooperatively with the Peltier devices and suitable control electronics provide for thermostatic control of the compliant housing.

The deflection imparted by the actuator to the housing is greatest at the center of the housing and tends to zero at the point or points where the housing is rigidly fixed to the counter mass. The ports which are located adjacent to a point where the housing is fixed remain substantially undeflected. This allows for convenient attachment to the ports of fittings, piping, heat exchangers, pumps, syringes, or other ancillary equipment without concern for damping, parasitic resonance or other influence to the motion of the oscillators.

Figure 2:
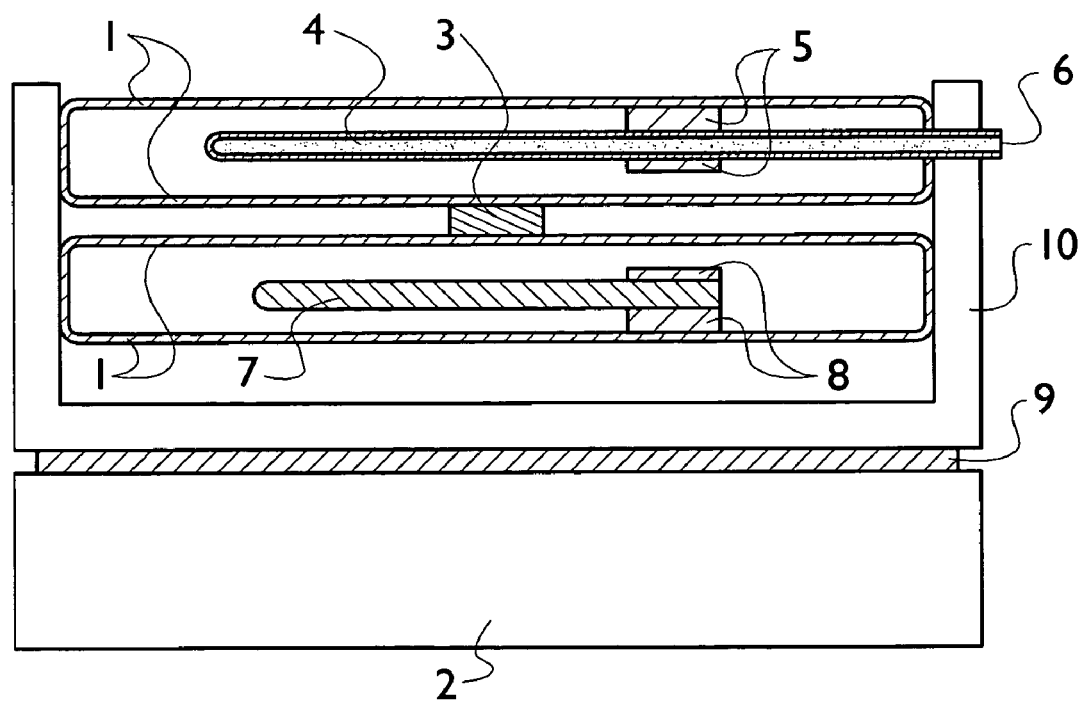
FIG. 2 depicts a schematic view of a second embodiment of the invention in which the compliant housing is decomposed into a system comprising a bracket and two independent compliant housings symmetrically disposed relative to the actuator.

Referring to FIG. 2, in this embodiment each half of housing 1 is implemented as a separate housing symmetrically disposed relative to the actuator. The housings are attached to a common bracket 10. With appropriate modification the description given for FIG. 1 applies similarly.

In FIG. 3, which is a cross section through either of the embodiments shown in FIG. 1 or FIG. 2, actuator 3 is piezoelectric element which acts in compression against compliant housing 1.

In FIG. 4, actuators 3 are piezoelectric elements which act in tension on bands 11 imparting motion to compliant housing 1. Bands 11 may be made of a transparent material so as not to impede the view of the oscillator during operation.

In FIG. 5 the actuator 3 is a piezoelectric element which imparts a bending action in armature 12. Armature 12 transmits motion to compliant housing 1.

Referring to FIG. 6, in this alternate embodiment of the current invention oscillator supports 5 and 8 are rigidly mounted to bracket 10. Bracket 10 is in turn rigidly mounted through Peltier device 9 to counter mass 2. Due to the rigid mounting of the oscillator supports relative to the counter mass, this arrangement can achieve a higher quality factor oscillation than that of the embodiments of FIGS. 1 and 2. Motion is imparted to oscillators 4 and 7 through an actuator comprising piezoelectric element 3 and flexible links 11 and 12. Rigid mounting of the oscillator supports also allows for improved thermal conduction between the oscillators and bracket 10.

Additionally, a reference oscillator of known type is employed in a manner wherein it is also excited by the balanced motion of the housing.

Figure 8:
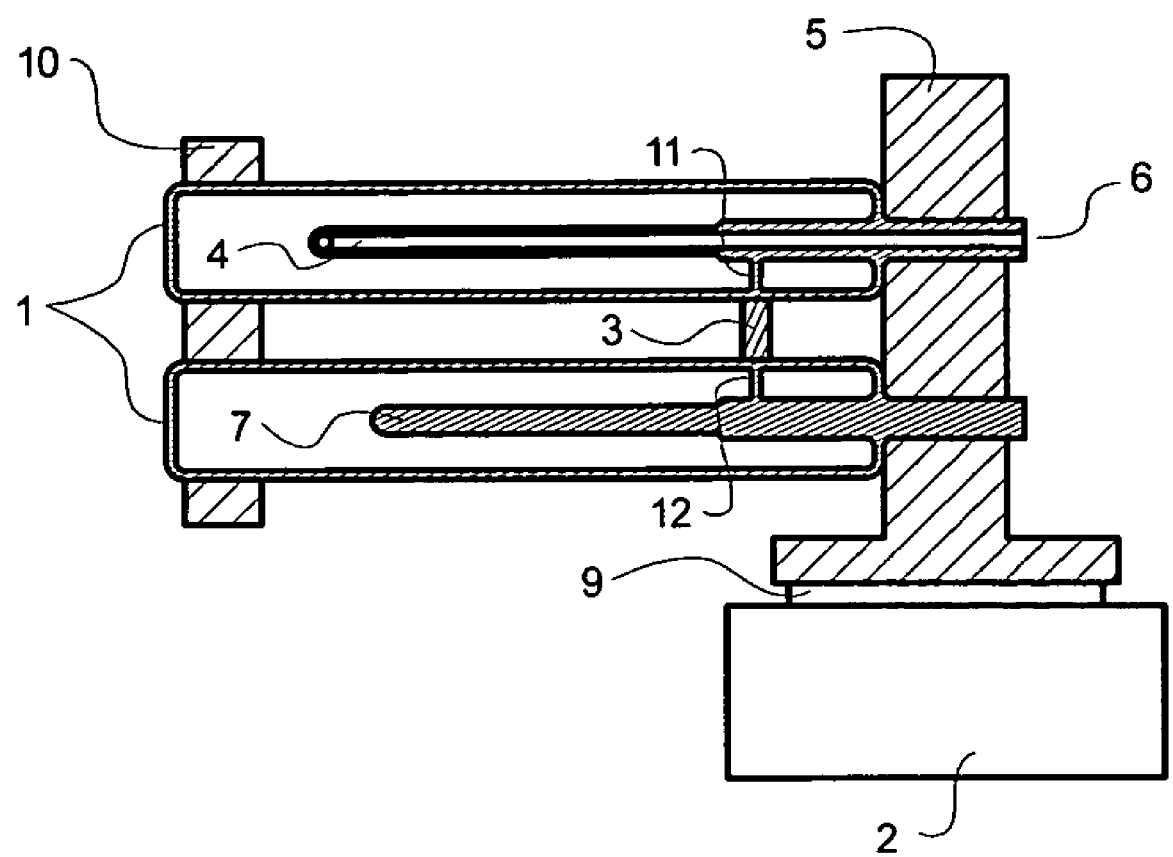
FIG. 8 is another exemplary embodiment of the present invention.

FIG. 7 depicts an alternative embodiment of the present invention in which the oscillator is mounted on the support in a slightly different manner as compared with FIG. 6. Specifically, the oscillator section narrows as shown and is inserted though a bore in the support 5, and deformity in the housing is transferred to oscillatory motion via linkages 11 and 12. The embodiment shown in FIG. 8 is similar to that in FIG. 7, but includes a different counter mass and support, as shown.

Those skilled in the art will recognize that the invention is not limited to the details of the embodiments, which are given here for the purpose of illustration. The concepts disclosed may be embodied in other specific forms without departing from the essence of the invention.

The invention claimed is:

1. An apparatus for measuring the density of fluids comprising:
    at least one actuator;
    a countermass;
    a housing or system of housings having at least one wall, fixed with respect to said countermass, acted upon by said at least one actuator, such that the center of mass of said housing or system of housings is not moved with respect to the countermass by the operation of said at least one actuator;
    and a hollow oscillator filled with a sample under test mounted on a support disposed within said housing or system of housings, said sample under test caused to oscillate by said actuator causing flexing of said at least one wall.

2. The apparatus of claim 1 further comprising temperature control means disposed between said housing or system of housings and said countermass.

3. The apparatus of claim 2 wherein said temperature control means is a Peltier device.

4. The apparatus of claim 1 wherein said at least one actuator is not connected to said support of said hollow oscillator.

5. The apparatus of claim 1 wherein said at least one actuator is a piezoelectric element.

6. The apparatus of claim 5 wherein said piezoelectric element acts in compression against said housing or system of housings.

7. The apparatus of claim 5 wherein said piezoelectric element acts in tension against a band for imparting force against said housing or system of housings.

8. The apparatus of claim 7 wherein said band comprises a transparent section.

9. An apparatus for measuring the density of fluids comprising:
    at least one actuator;
    a housing or system of housings having at least one wall, acted upon by said at least one actuator, such that the center of mass of said housing or system of housings remains substantially fixed in space when acted upon by said actuator;
    and a hollow oscillator filled with a sample under test mounted on a support disposed within said housing or system of housings, said sample under test caused to oscillate by said actuator causing flexing of said at least one wall; and
    a reference oscillator for improving the accuracy of measurements made at temperatures differing from a calibration temperature.

10. The apparatus of claim 9 wherein said reference oscillator is driven in opposition to said hollow oscillator.

11. An apparatus comprising an actuator disposed between and in contact with two housings, the actuator imparting a deformity upon the housings, the deformity being transferred to an oscillator within each housing by a linkage placed between an inner wall of each housing and said oscillator within said each housing.

12. Apparatus of claim 11 wherein a portion of each housing is positioned within a bore in a support.

13. The apparatus of claim 12 wherein the portion of each housing that is positioned within said bore is narrower than a portion of each housing outside of said bore.

14. The apparatus of claim 13 wherein said deformity is periodically imparted in equal and opposite directions upon two different housings.

15. The apparatus of claim 14 wherein a first of said oscillators is longer than a second of said oscillators.

16. The apparatus of claim 12 wherein walls of said oscillators vary in thickness along the length thereof.

* * * * *